US00PP31208P2

(12) United States Plant Patent
Korlipara

(10) Patent No.: US PP31,208 P2
(45) Date of Patent: Dec. 10, 2019

(54) ***GEUM* PLANT NAMED 'TNGEUPP'**

(50) Latin Name: ***Geum* hybrid**
Varietal Denomination: TNGEUPP

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,014

(22) Filed: Sep. 11, 2018

(51) Int. Cl.
*A01H 5/02* (2018.01)
*A01H 6/74* (2018.01)

(52) U.S. Cl.
USPC ..... Plt./263.1

(58) Field of Classification Search
USPC ..... Plt./263.1
CPC ..... A01H 5/02; A01H 5/00; A01H 6/74
See application file for complete search history.

(56) References Cited

PUBLICATIONS

Spring Mountain Growers on Facebook 2018, retrieved on Jun. 18, 2019, retrieved from the Internet at https://www.facebook.com/springmountaingrowers/photos/the-great-list-is-geum-petticoats-peach-back-in-january-i-saw-an-write-up-in-sun/1687772744647039/, one page. (Year: 2018).*

* cited by examiner

*Primary Examiner* — June Hwu
(74) *Attorney, Agent, or Firm* — Klarquist Sparkman, LLP

(57) ABSTRACT

A new and distinct *Geum* plant named 'TNGEUPP' characterized by flowers light yellow with rose-red edges and tints giving it a peach tone, with older flowers tinted rose-red, double flowers, good flower size, heavy blooming, dense, deep green foliage with attractive leaves, a compact, mounding habit, heavy spring bloom with repeat bloom throughout the summer, and excellent vigor.

1 Drawing Sheet

Botanical designation: *Geum* hybrid.
Variety denomination: 'TNGEUPP'.
Trademark designation: Pretticoats™ Peach

BACKGROUND OF THE INVENTION

The present invention relates to a new and distinct cultivar of *Geum* plant given the name 'TNGEUPP'. *Geum* is in the family Rosaceae. The new cultivar was bred using unknown, unnamed proprietary plants. The new cultivar was selected for its superior habit and flowering.

Compared to *Geum* 'Cosmopolitan' (U.S. Plant Pat. No. 24,982) the new cultivar has more yellow in the flower color and is more compact, with more and shorter flowering stems. In addition the new cultivar reblooms sporadically throughout the summer rather than being only spring blooming.

Compared to *Geum* 'Mai Tai' (U.S. Plant Pat. No. 22,433) the new cultivar is more compact, with more and shorter flowering stems. In addition the new cultivar reblooms sporadically throughout the summer rather than being only spring blooming.

SUMMARY OF THE INVENTION

The following traits have been repeatedly observed and are determined to be the unique characteristics of 'TNGEUPP'. These characteristics in combination distinguish 'TNGEUPP' as a new and distinct cultivar:

1. flowers light yellow with rose-red edges and tints giving it a peach tone, with older flowers tinted rose-red,
2. double flowers,
3. good flower size,
4. heavy blooming,
5. dense, deep green foliage with attractive leaves,
6. a compact, mounding habit,
7. heavy spring bloom with repeat bloom throughout the summer, and
8. excellent vigor.

This new cultivar has been reproduced by asexual propagation in Canby, Oreg., and has shown the foregoing characteristics and distinctions come true to form and are established and transmitted through succeeding propagations. Propagation is conducted in tissue culture, using standard micropropagation techniques by dividing terminal and lateral shoots. Each of the progeny exhibits identical characteristics to the original plant. The present invention has not been evaluated under all possible environmental conditions. The phenotype may vary with variations in environment without a change in the genotype of the plant.

BRIEF DESCRIPTION OF THE DRAWING

FIG. 1 shows a two-year-old *Geum* 'TNGEUPP' blooming in the garden in April in Canby, Oreg.

FIG. 2 shows a two-year-old *Geum* 'TNGEUPP' growing in the garden in April in Canby, Oreg.

DETAILED PLANT DESCRIPTION

The following is a detailed description of the new *Geum* cultivar based on observations of a two-year-old specimens growing in the garden in full sun under typical outdoor conditions in late April in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 2007, 5$^{th}$ edition.

Plant:

*Type*.—Herbaceous perennial.

*Hardiness*.—USDA Zone 5-9.

*Size*.—30 cm wide and 25 cm tall to top of the foliage, 30 cm to top of flowers.

*Form*.—Mound with 50 to 60 crowns.

*Persistence*.—Dies down to the crown in winter.

*Vigor*.—Excellent.

*Stem*.—None.

Leaf:

*Type*.—Simple, rosulate.

*Arrangement*.—Basal rosette.

*Surface texture*.—Pubescent on both sides.

*Venation*.—Pinnate and impressed.

*Petiole and rachis*.—Grows to 10.5 cm long and 0.3 wide (0.6 mm wide at base), pubescent, Yellow Green 147D, petiole base clasping.

*Rosulate leaves*.—Lyrate-pinnate, 9-foliate, with leaflets in pairs in declining size below the terminal leaflet (smallest to 0.6 mm wide, 0.9 mm long); terminal leaflet largest, rhomboid, grows to 4.3 cm long and 6 cm wide, 3-7 lobed, truncate base, margins irregularly serrate, tip obtuse to notched to acute; top lateral leaflets, 3.5 mm wide, 3 mm long, irregularly obovate, with 2 lateral shallow lobes, margins serrate, opposite, tips acute to obtuse, bases cuneate, sessile.

*Color*.—Topside Green 137A including veins, bottom side Yellow Green 147B with veins 146C.

Inflorescence:

*Description*.—In cymes, 1 to 3 cymes from each crown with 2 to 6 flowers per cyme.

*Size of inflorescence*.—Grows to 11 cm wide and 13 cm long.

*Flowering stem attitude*.—Upright to semi-upright.

*Peduncle*.—Grows to 17 cm tall and 4 mm wide, pubescent, Yellow Green 147C where shaded and Greyed Orange 166A where exposed to sun.

*Peduncle leaves*.—Lyrate, petiolate with petioles to 8 mm long, blade grows to 3.4 cm long and 4 cm wide, 3-lobed, serrate, tips attenuate, base cuneate, pubescent on both sides; stipules large adnate to petiole, foliar, grow to 1 cm long and 1.5 cm wide, irregularly incised, pubescent on both sides; leaves and stipules topside Green 137A including veins, bottom side Yellow Green 146B with veins 146C.

*Rachis*.—About 4.5 cm long, 2 mm wide, pubescent, Greyed Orange 166A.

*Pedicel*.—Variable in length, 2 cm to 3.5 cm long and 1 mm wide, Greyed Purple 187B, Greyed Orange 166A.

Flower bud:

*Size*.—15 mm long and 10 mm wide.

*Shape*.—Conic, nodding.

*Surface*.—Pubescent.

*Color*.—Greyed Purple 183A.

Flower:

*Type*.—Actinomorphic, double.

*Size*.—30 mm wide and 15 mm deep.

*Flower attitude*.—Side-facing.

*Corolla description*.—Usually 15 petals, broadly obovate in shape, grows to 15 mm deep and 14 mm wide, margins slightly undulate, tip notched to sometimes obtuse, base truncate, with claw (2 to 4 mm long), glabrous on both sides, top side Yellow 11D with margins Red Purple 61A, bottom side Yellow 11D tinted Red Purple 61A; older flowers between Yellow-Orange 18D and Red 38D with margins Red Purple 61A.

*Calyx description*.—5 main sepal lobes alternating with 5 smaller lobes, stellate, 10 mm deep and 34 mm wide overall, Greyed Green 195A inside Greyed Purple 187A on base to Yellow Green 148C tinted Greyed Purple 187A on lobes, pubescent outside and glabrous inside, lobes ovate, margins entire, tips acuminate and reflexed, main lobes 7 mm long and 5 mm wide, smaller lobes 7 mm long and 1.5 mm wide.

*Pistil description*.—1 in number, 9 mm long and 7 wide, ovary 5 mm long and 4 mm wide, Yellow Green 146C and covered with white hairs; about 100 hair-like styles and stigmas, styles 5 mm long, not geniculately jointed, Yellow Green 146C tinted Greyed Orange 175A near stigma; stigmas Greyed Orange 175A.

*Stamen description*.—About 120, 5.4 mm long, filaments 5 mm long, Yellow Green 145C, anthers 0.4 mm long, Yellow 8A, pollen Yellow 13B.

*Fragrance*.—None.

*Lastingness*.—Each flower last approximately one week in summer and up to two weeks in cool weather.

*Bloom time*.—April to May with rebloom through September.

Fruit: None.

Seed: None, sterile.

Disease and pests: The new cultivar is typical to the genus. No known resistances to pests or diseases.

I claim:

1. A new and distinct *Geum* plant as herein illustrated and described.

* * * * *

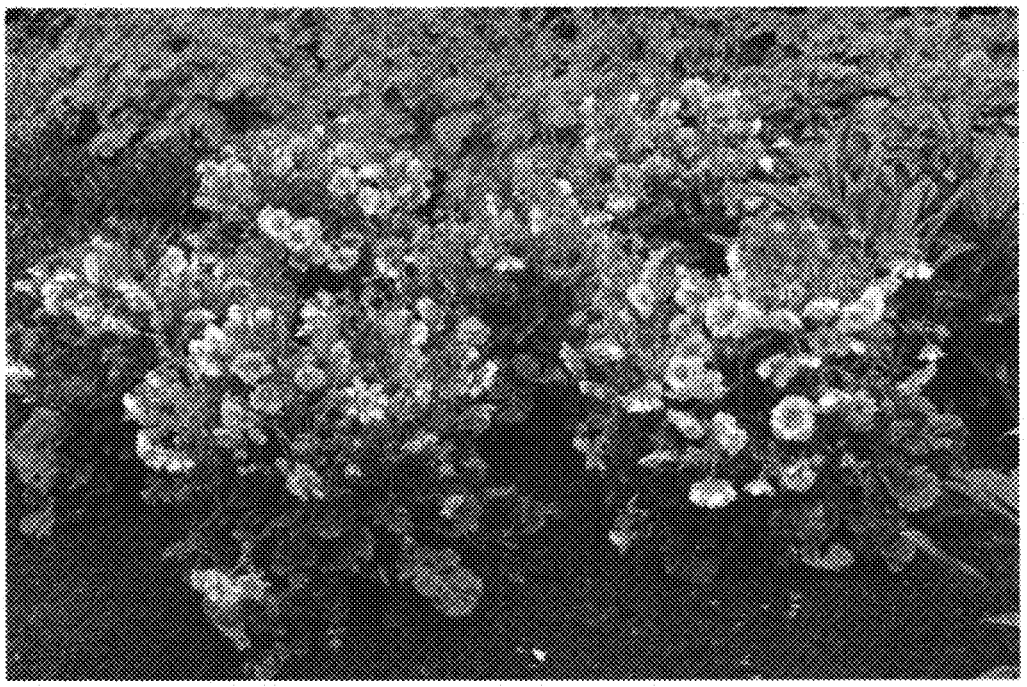

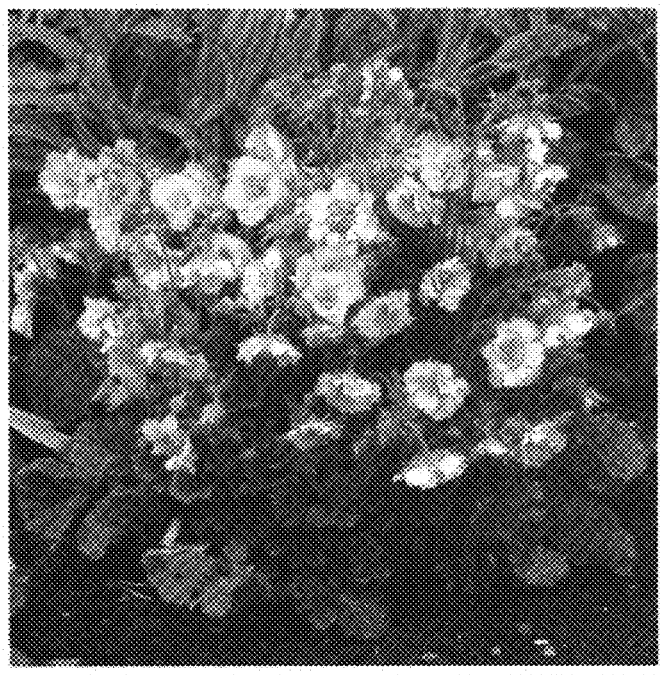
Fig.1 Left
Fig. 2 Below